US006815167B2

(12) United States Patent
Crothers et al.

(10) Patent No.: US 6,815,167 B2
(45) Date of Patent: Nov. 9, 2004

(54) AMPLIFICATION OF DNA TO PRODUCE SINGLE-STRANDED PRODUCT OF DEFINED SEQUENCE AND LENGTH

(75) Inventors: Donald M. Crothers, Northford, CT (US); Carol Koenigsberger, San Diego, CA (US)

(73) Assignee: GeneOhm Sciences, San Diego, CA (US)

( * ) Notice: Subject to any disclaimer, the term of this patent is extended or adjusted under 35 U.S.C. 154(b) by 138 days.

(21) Appl. No.: 10/138,067

(22) Filed: May 1, 2002

(65) Prior Publication Data

US 2003/0207279 A1 Nov. 6, 2003

Related U.S. Application Data

(60) Provisional application No. 60/376,141, filed on Apr. 25, 2002.

(51) Int. Cl.[7] .................. C12Q 1/68; C12P 19/34; C07H 21/02; C07H 21/00
(52) U.S. Cl. .............. 435/6; 435/91.2; 536/23.1; 536/25.32; 536/25.4; 536/26.6
(58) Field of Search .............. 435/6, 91.2; 536/23.1, 536/25.32, 25.4, 26.6

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,888,286 A | 12/1989 | Crea | 435/172.3 |
| 5,518,900 A | 5/1996 | Nikiforov et al. | |
| 5,849,542 A | 12/1998 | Reeve et al. | 435/91.2 |

FOREIGN PATENT DOCUMENTS

| | | | |
|---|---|---|---|
| EP | 0 971 039 A2 | 1/2000 | C12Q/1/60 |

OTHER PUBLICATIONS

Higuchi et al, "Production of Single–Stranded DNA Templates by Exonculeases Digestion Following the Polymerase Chain Reaction" (1989) *Nucleic Acids Research*, vol. 17, No. 14 p. 5865.

Sugisaki et al., "New Restriction Endoncleases from Flavobacterium Okeanokoites (FokI) and Micrococcus Lutens (MluI)", (1981) *Gene* vol. 16, pp. 73–78.

Shchepinov et al.: Oligonucleotide Dendrimers: Synthesis and Use as Polylabelled DNA Probes (1997) *Nucleic Acids Research* vol. 25, No. 22 pp. 4447–4454.

Lizardi et al., "Mutation Detection and Single–Molecule Counting Using Isothermal Rolling–Circle Amplification" (1998) *Nature Genetics* vol. 19, pp. 225–232.

Szybalski, "Universal Restriction Endonucleases: Designing Novel Cleavage Specificities by Combining Adapter Oligodeoxynucleotide and Enzyme Moieties" (1985) *Gene* vol. 40, pp. 169–173.

Podhajska et al., "Conversion of the FokI Endonuclease to a Universal Restriction Enzyme: Cleavage of Phage M13mp7 DNA at Predetermined Sites" (1985) *Gene* vol. 40, pp. 175–182.

*Primary Examiner*—Kenneth R. Horlick
*Assistant Examiner*—Joyce Tung
(74) *Attorney, Agent, or Firm*—Knobbe Martens Olson & Bear, LLP

(57) ABSTRACT

The present disclosure relates to methods for generating single-stranded DNA molecules of defined sequence and length. Specifically, a region of template containing target sequence is amplified by PCR or RCA, exogenous sequence is introduced by primers or probes used in amplification, double-stranded amplification products are converted to single-stranded amplification products, and single-stranded amplification products are trimmed to produce short single-stranded DNA molecules of defined sequence and length.

71 Claims, 8 Drawing Sheets

AMPLIFICATION OF DNA TO PRODUCE SINGLE-STRANDED PRODUCT OF DEFINED SEQUENCE AND LENGTH

RELATED APPLICATIONS

This application claims priority to U.S. Provisional Application No. 60/376,141, filed Apr. 25, 2002.

FIELD OF THE INVENTION

The present disclosure relates generally to methods for generating single-stranded DNA molecules of defined sequence and length from template containing a target nucleotide sequence. Specifically, the present disclosure provides a method for generating short single-stranded DNA molecules of defined sequence and length by linear or non-linear amplification of a template using specially designed primers or probes, conversion of double-stranded amplification products into single-stranded amplification products if necessary, and trimming single-stranded amplification products to yield the desired DNA molecule of defined sequence and length.

BACKGROUND OF THE INVENTION

Amplification of Target Sequences

A number of methods have been developed for amplification of target nucleotide sequences in nucleic acid templates. These include the polymerase chain reaction (PCR), rolling circle amplification (RCA), ligase chain reaction (LCR), self-sustained sequence replication (3SR), nucleic acid sequence based amplification (NASBA), and strand displacement amplification (SDA).

Current methods of PCR amplification involve the use of two primers which hybridize to the regions flanking target nucleotide sequence, such that DNA replication initiated at the primers will replicate the target nucleotide sequence. By separating the replicated strands from the template strand with a denaturation step, another round of replication using the same primers can lead to many-fold amplification of the target nucleotide sequence.

Rolling circle amplification (RCA) is an isothermal amplification method in which a circularizable single-stranded probe is hybridized to a template such as RNA or denatured DNA at regions flanking the target nucleotide sequence, the strand is circularized using primer extension and/or ligation, sequences in the circle are then selectively amplified, and optionally, non-circular products are removed by digestion.

Linear and Nonlinear Amplification of Target Sequences

Amplification of target sequences may be carried out in linear or non-linear mode, for example as described in EP 0971039 to Rabanni et al. Linear amplification of target sequences may be used when a starting mixture contains a large number of copies of a target sequence. Generally, linear amplification utilizes a single initial primer, probe, or other nucleic acid construct to carry out the amplification process.

Non-linear amplification of target sites is often used when the number of copies of a target sequence present in the starting mixture is small. Non-linear amplification results in exponential growth in the number of gene copies present. PCR and RCA, especially RCA in the branching mode, can be used effectively in the non-linear amplification mode. (Lizardi et al., 1998, *Nature Genetics* 19:225–232)

Generation of Single Stranded DNA

Many amplification methods generate double-stranded amplification products, while many applications require single-stranded DNA molecules containing the target sequence. Double-stranded DNA can be converted to single-stranded DNA by separating the strands or by removing one strand of the duplex. Strands of a duplex can be separated by thermal or chemical methods of disrupting interstrand bonds. Removing one strand allows recovery of the desired strand and elimination of its complement. One strategy for selectively removing one strand of a DNA duplex is to use exonuclease digestion, preferably 5'→3' exonuclease digestion, where one strand is protected from attack by the exonuclease.

For example, U.S. Pat. No. 5,518,900 to Nikiforov et al. describes modifying one of two PCR primers used for amplification by incorporating phosphorothioate nucleotide derivatives in the 5' end of the modified primer, rendering it resistant to exonuclease digestion. After amplifying target sequences using PCR, the double-stranded amplification product is subjected to exonuclease digestion. The unprotected strand is preferentially digested by a 5'→3' exonuclease, leaving a single-stranded product consisting of the other strand.

In an alternate approach, Shchepinov et al. uses branched PCR primers that are resistant to 5'-exonuclease digestion, with the result that exonuclease digestion of the double-stranded amplification products gave single strands protected from digestion by the exonuclease-resistant branched primers. (Shchepinov et al., 1997, *Nuc Acids Res* 25:4447–4454) Disadvantages of this method are that branched primers are difficult to synthesize and the resulting PCR products are branched.

Another approach to generating single-stranded DNA uses phosphorylation of the 5' end of one strand of a double-stranded amplification product to produce a preferred lambda exonuclease substrate. (Higuchi et al., 1989, *Nuc Acids Res* 25: 5685) This method allows selective degradation of the phosphorylated strand and recovery of the nonphosphorylated strand.

Generation of Short Single-stranded DNA Molecules

Short single-stranded DNA molecules of defined sequence and length are needed for applications such as arrays, where the desirable size range is about 45 nucleotides or less. Although methods for generating single-stranded DNA molecules are known in the art, these methods do not necessarily generate small molecules of 45 nucleotides or less. For example, the methods discussed above for generating single-stranded DNA do not provide short single-stranded DNA molecules of defined sequence and length. U.S. Pat. No. 5,518,900 to Nikiforov et al. teaches methods for generating single-stranded DNA molecules from double-stranded PCR amplification products, but the resulting PCR products are typically longer than 45 nucleotides. The method of Shchepinov et al. produces branched PCR products that are typically longer than 45 nucleotides. (Shchepinov et al., 1997, *Nuc Acids Res* 25:4447–4454) Likewise, the method of Higuchi et al. yields single-stranded DNA products that are not in the desired size range. (Higuchi et al. 1989, *Nuc Acids Res* 17: 5865)

Shaw and Mok disclose cleaving single-stranded DNA into fragments by interaction with a specially designed oligodeoxyribonucleotide adaptor and the class-IIN restriction endonuclease, XcmI. (Shaw and Mok, 1993, *Gene* 133:85–89) After hybridizing to the target DNA and addition of XcmI, template DNA is specifically cleaved to near completion; however, hairpin structures on the template close to the hybridization site reduce the efficacy of cleavage.

SUMMARY OF THE INVENTION

The invention described herein is directed to methods for generating a single-stranded DNA molecule of defined sequence and length, where the method includes amplification, conversion, and trimming steps. In accordance with one aspect of the invention, amplification of a template having at least one target nucleotide sequence is directed by one or more primers having at least one exogenous nucleotide sequence not present in the target nucleotide sequence, where the amplification step generates amplification products with at least one target nucleotide sequence and at least one exogenous nucleotide sequence introduced by the primer. In accordance with another aspect of the invention, a conversion step may be performed. When the amplification step generates double-stranded amplification products, the method includes a conversion step wherein each double-stranded amplification product is converted to a single-stranded amplification product. When the amplification step generates single-stranded amplification products, the conversion step is not required. In accordance with another aspect of the invention, the single-stranded amplification product is trimmed to generate a single-stranded DNA molecule of defined sequence and length.

In accordance with one aspect of the invention, polymerase chain reaction (PCR) is used for the amplification step to produce double-stranded amplification products. In one embodiment, multiplex PCR may be used. The amplification step can be carried out in linear or non-linear mode. The template for amplification may be genomic DNA, cDNA, or RNA.

In accordance with another aspect of the invention, rolling circle amplification (RCA) is used for the amplification step. In various embodiments, RCA may produce double-stranded or single-stranded amplification products. In one embodiment, RCA in the linear mode is used to generate single-stranded amplification products. The amplification step can be carried out in linear or non-linear mode. The template for amplification may be genomic DNA, cDNA, or RNA, including mRNA.

In one embodiment, primers for the amplification step may have an addressable ligand such as biotin attached to the primer. In another embodiment, exogenous nucleotide sequence introduced by primers used in the amplification step may contain self-complementary sequences that form hairpin structures. These self-complementary sequences that form hairpin structures may contain at least one restriction enzyme recognition site for a restriction enzyme involved in the trimming step, and suitable restriction enzymes include Type II restriction enzymes such as EcoRI, or Type IIS restriction enzymes such as FokI.

In another embodiment, exogenous nucleotide sequence(s) introduced by primers include sequence(s) that can form a recognition site for a restriction enzyme involved in said trimming step, where the restriction enzyme recognition site is formed upon addition of at least one auxiliary oligonucleotide. Suitable restriction enzymes include Type II restriction enzymes such as EcoRI, or Type IIS restriction enzymes such as FokI. In another embodiment, the auxiliary oligonucleotide includes at least one sequence having an addressable ligand such as biotin attached.

In accordance with another aspect of the invention, the conversion step may be carried out by digesting one strand of a double-stranded amplification product using a 5'→3' exonuclease such T7 or lambda exonuclease, where the amplification product includes at least one target nucleotide sequence and at least one exogenous nucleotide sequence introduced by a primer during the amplification step. In a preferred embodiment, the exogenous nucleotide sequence introduced by a primer includes modified nucleotides that confer resistance to digestion using 5'→3' exonuclease, for example where the nucleotides are phosphorothioate derivates. In another preferred embodiment, the exogenous nucleotide sequence introduced by a primer includes modified nucleotides that confer sensitivity to digestion using 5'→3' exonuclease, for example where the modified nucleotides are phosphorylated.

In accordance with another aspect of the invention, a method is provided for generating a single-stranded DNA molecule of defined sequence and length which avoids the exonuclease step and a requirement for auxiliary oligonucleotides. The method includes amplifying a template containing at least one target nucleotide sequence, where the amplification is directed by at least one primer having at least one exogenous nucleotide sequence not present in the target nucleotide sequence, generating a plurality of double-stranded amplification products having at least one target nucleotide sequence and at least one exogenous nucleotide sequence introduced by at least one primer, then nicking each double stranded amplification product at one end of a defined sequence and cleaving the double stranded amplification product at the other end of a defined sequence to generate a DNA molecule of defined sequence and length, and finally, separating the single stranded DNA molecule of defined sequence and length from the remainder of the amplification product that includes its complement and the primer duplexes of the amplification product. The single stranded DNA molecule of defined sequence and length can be recovered for further use. In accordance with one aspect, the single stranded DNA molecule of defined sequence and length is separated from the remainder of the amplification product by heating under conditions that allow the single stranded DNA molecule of defined sequence and length to separate from its complement while leaving the the primer duplexes of the amplification product intact. In accordance with another aspect, the primers include an addressable ligand attached to the primer. In one embodiment, the adressable ligand is biotin, and the remainder of the amplification product can be removed by attachment to magnetic beads carrying streptavidin that binds to biotin labels attached to the 5' end of at least one primer.

In accordance with the methods of the present invention, the single-stranded DNA molecule of defined sequence and length generated by the present invention may be between 10 and 100 nucleotides, or between 10 and 50 nucleotides in length. In one embodiment, the single-stranded DNA molecule of defined sequence and length is 15 nucleotides in length. In another embodiment, the single-stranded DNA molecule of defined sequence and length is 17 nucleotides in length. In yet another embodiment, the single-stranded DNA molecule of defined sequence and length is 21 nucleotides in length. In yet another embodiment, the single-stranded DNA molecule of defined sequence and length is 30 nucleotides in length.

Another aspect of the present invention is directed to methods for identifying an organism or individual using some or all of the following steps: 1) obtaining template having at least one target nucleotide sequence; 2) amplifying the template in an amplification reaction directed by at least one primer having an exogenous nucleotide sequence not present in the target nucleotide sequence; 3) generating amplification products having at least one target nucleotide sequence and at least one exogenous nucleotide sequence introduced by a primer; 4) converting double-stranded amplification products to single-stranded amplification products; trimming each single-stranded amplification product to generate a single-stranded DNA molecule of defined sequence and length; 5) determining the mass or nucleotide sequence of each single-stranded DNA molecule of defined sequence and length; and 6) using at least one mass or nucleotide sequence determination of at least one single-stranded DNA molecule of defined sequence and length to identify at least one organism or individual. In accordance with another aspect of the invention, it is understood that if the amplification step produces single-stranded amplification products, the conversion step is not required. In one embodiment, mass spectroscopy may be used to determine the mass or nucleotide sequence of each single-stranded DNA molecule of defined sequence and length. In another embodiment, a multiplicity of individuals or organisms is identified by this method.

DETAILED DESCRIPTION OF THE PREFERRED EMBODIMENT

The present disclosure provides methods for generating single-stranded DNA molecules having defined sequence and length from a template such as genomic DNA, cDNA, or RNA. Advantageously, the methods disclosed and claimed herein enable production of large numbers of single-stranded amplification products containing target nucleotide sequence, which are trimmed to produce single-stranded DNA molecules having defined sequence and length and further, where the entire procedure may, if desired, be performed in a single reaction vessel.

The methods disclosed herein include, but are not limited to, amplification of a template including at least one target nucleotide sequence, using at least one primer or probe having exogenous nucleotide sequence not found in the target nucleotide sequence, generating amplification products including at least one target nucleotide sequence and at least one exogenous nucleotide sequence, converting double-stranded amplification products to single-stranded amplification products if necessary, and trimming single-stranded amplification products to yield single-stranded DNA molecules of defined sequence and length. Advantageously, the methods disclosed herein provide a strategy for generating amplification products including at least one target nucleotide sequence and at least one exogenous nucleotide sequence involved in post-amplification processing of the amplification product. Optionally, at least one exogenous nucleotide sequence, which may include modified bases, is involved in conversion of double-stranded amplification products to single-stranded amplification products. Preferably, at least one exogenous nucleotide sequence is involved in restriction endonuclease-mediated trimming of single-stranded amplification products to generate single-stranded DNA molecules having defined sequence and length.

Figure 1:
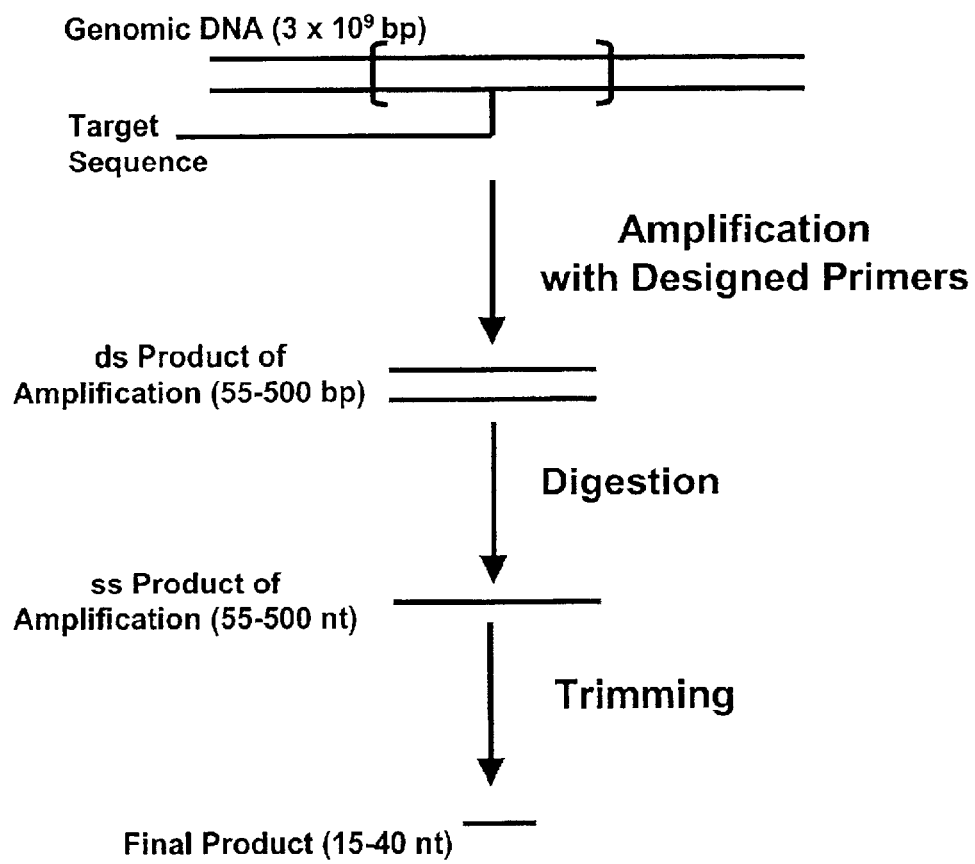
FIG. 1. Outline of the method, showing amplification to produce double-stranded molecules, digestion of one strand, and trimming the resulting single strand to the final length.

In accordance with one aspect of the present invention, the methods disclosed herein provide amplification methods to generate double-stranded amplification products that are converted to single-stranded amplification products that are then trimmed to yield single-stranded DNA molecules of defined sequence and length (FIG. 1). Advantageously, the methods disclosed herein provide a strategy for generating double-stranded amplification products including at least one target nucleotide sequence and at least one exogenous nucleotide sequence involved in post-amplification processing of double-stranded amplification products, including conversion to single-stranded amplification products and subsequent trimming of single-stranded amplification products. In a preferred embodiment, a double-stranded amplification product has two exogenous nucleotide sequences, one at each end of the product, where the exogenous nucleotide sequences are involved in post-amplification processing of double-stranded amplification products.

In accordance with another aspect of the present invention, the methods disclosed herein provide amplification methods to generate single-stranded amplification products that are then trimmed to yield single-stranded DNA molecules of defined sequence and length. Advantageously, the methods disclosed herein provide a strategy for generating single-stranded amplification products including at least one target nucleotide sequence and at least one exogenous nucleotide sequence involved in post-amplification trimming of single-stranded amplification products. In a preferred embodiment, a single-stranded amplification product contains one target nucleotide sequence and has two exogenous nucleotide sequences, one at the 3' and one at the 5' end of the product, where the exogenous nucleotide sequences are involved in post-amplification processing of single-stranded amplification products. In another preferred embodiment, a single-stranded amplification product contains more than one target nucleotide sequence and each target nucleotide sequence is flanked by exogenous nucleotide sequences, where the exogenous nucleotide sequences are involved in post-amplification processing of single-stranded amplification products.

As used herein, "template" refers to all or part of a polynucleotide containing at least one target nucleotide sequence. As used herein, a "target nucleotide sequence"

includes the nucleotide sequence of the final product having defined sequence and length, and may include other nucleotide sequences that are removed during post-amplification processing of the amplification product. Nucleotide sequences that are found in the target nucleotide sequence and later removed may include binding sites (annealing sites) for primers or probes, nucleotides involved in conversion of double-stranded DNA to single-stranded DNA, or sequences useful as recognition and/or cleavage sites for restriction endonucleases. An "exogenous nucleotide sequence" as used herein, refers to a sequence introduced by primers or probes used for amplification, such that amplification products will contain exogenous nucleotide sequence and target nucleotide sequence in an arrangement not found in the original template from which the target nucleotide sequence was copied. As used herein, an "auxiliary oligonucleotide" is a DNA sequence that can be used to create a restriction digestion site by binding to one or more sequences in the single-stranded amplification products. In a preferred embodiment, the auxiliary oligonucleotides are complementary to one or more parts of the single-stranded amplification products, and duplex formation creates a restriction site that enables trimming of the single-stranded amplification product to the final desired size. Auxiliary oligonucleotides and primers may contain chemical modifications to enable the trimmed single-stranded product to be separated from primers and auxiliary oligonucleotides. In a preferred embodiment, the chemical modification is an addressable ligand permitting recovery of a molecule containing the ligand. In a more preferred embodiment, the addressable ligand is a biotin residue.

In accordance with another aspect of the present invention, the template may be any polynucleotide suitable for amplification, where the template contains at least one target nucleotide sequence to be amplified. Suitable templates include DNA and RNA molecules, and may include polynucleotides having modified bases. Preferably, templates are genomic DNA, cDNA, or RNA molecules. In another preferred embodiment, methods disclosed herein can be used to amplify RNA templates directly, without reverse-transcribing the RNA template into cDNA.

In accordance with another aspect of the present invention, the methods disclosed herein provide at least one double-stranded amplification product that is converted to a single-stranded form that is then trimmed to yield at least one single-stranded DNA molecule of defined sequence and length. Advantageously, the method disclosed herein provides a strategy for generating a single-stranded amplification product containing a region having a target nucleotide sequence and at least one exogenous nucleotide sequence that promotes restriction endonuclease-mediated trimming of the single-stranded amplification product to generate a the desired single-stranded DNA molecule of defined sequence and length.

Amplification of Polynucleotide Templates

In accordance with one aspect of the invention as disclosed herein, amplification of templates is carried out using well-known methods to generate amplification products including at least one target nucleotide sequence and at least one exogenous sequence involved in post-amplification processing of the amplification product without a significant effect on the amplification itself. Preferably, post-amplification processing includes, but is not limited to, conversion of double-stranded amplification products to single-stranded amplification products, and trimming of single-stranded amplification products to generate a single-stranded DNA molecule of defined sequence and length.

Suitable templates include DNA and RNA molecules such as genomic DNA, cDNA, and mRNA. Linear or exponential (nonlinear) modes of amplification may be used with any suitable amplification method, where choice of mode is made by one of skill in the art depending on the circumstances of a particular embodiment. Methods of amplification include, but are not limited to, use of polymerase chain reaction (PCR) and rolling circle amplification (RCA) to amplify polynucleotide templates.

Polymerase Chain Reaction

The polymerase chain reaction (PCR) is a method for in vitro amplification of DNA. PCR uses multiple rounds of primer extension reactions in which complementary strands of a defined region of a DNA molecule are simultaneously synthesized by a thermostable DNA polymerase. During repeated rounds of these reactions, the number of newly synthesized DNA strands increases exponentially such that after 20 to 30 reaction cycles, the initial template DNA will have been replicated several thousand-fold or million-fold. Methods for carrying out different types and modes of PCR are thoroughly described in the literature, for example in "*PCR Primer: A Laboratory Manual*" Dieffenbach and Dveksler, eds. Cold Spring Harbor Laboratory Press, 1995, and by Mullis et al. in patents (e.g., U.S. Pat. Nos. 4,683,195, 4,683,202 and 4,800,159) and scientific publications (e.g. Mullis et al. 1987, *Methods in Enzymology*, 155:335–350) where the contents of each reference are hereby incorporated by reference in their entireties.

Briefly, PCR proceeds in a series of steps as described below. In the initial step of the procedure, double-stranded template (e.g., genomic DNA or cDNA) is isolated and heat, preferably between about 90° C. to about 95° C., is used to separate the double-stranded DNA into single strands (denaturation step). Cooling to about 55° C. allows primers to adhere to the target region of the template, where the primers are designed to bind to regions that flank the target nucleic acid sequence (annealing step). Thermostable DNA polymerase (e.g., Taq polymerase) and free nucleotides are added to create new DNA fragments complementary to the target region of the template via primer extension (extension step), to complete one cycle of PCR. This process of denaturation, annealing and extension is repeated numerous times, preferably in a thermocycler. At the end of each cycle, each newly synthesized DNA molecule acts as a template for the next cycle, resulting in the accumulation of many hundreds or thousands, Or even millions, of double-stranded amplification products from each template molecule.

In multiplex PCR, the assay is modified to include multiple primer pairs specific for distinct target nucleotide sequences of the same template, to allow simultaneous amplification of multiple distinct target nucleotide sequences and generation of multiple distinct single-stranded DNA molecules having the desired nucleotide sequence and length. For example, multiplex PCR can be carried out using the genomic DNA of an organism or an individual as the template, where multiplex PCR will produce multiple distinct single-stranded DNA molecules. The sequence of each distinct single-stranded DNA molecule having the desired nucleotide sequence and length can be determined, for example using mass spectroscopy to rapidly determine sequence, and the results can be used to identify an organism or an individual.

PCR generates double-stranded amplification products suitable for post-amplification processing. If desired, amplification products can be detected by visualization with agarose gel electrophoresis, by an enzyme immunoassay format using probe-based colorimetric detection, by fluorescence emission technology, or by other detection means known to one of skill in the art.

Primers for Amplification

In accordance with one aspect of the present invention, primers are utilized to permit amplification of a template containing a target nucleotide sequence and to introduce additional features into the amplification products. Each primer contains nucleotide sequence that is complementary to a region of target nucleotide sequence in the template, in order for each primer to bind (anneal) to the template. In a preferred embodiment, at least one primer contains exogenous nucleotide sequence 5' (upstream) of the primer sequence complementary to the primer-binding target nucleotide sequence, with the result that each amplification product contains exogenous nucleotide sequence introduced by the primer. Preferably, two primers are used, where each primer introduces exogenous nucleotide sequence that allow post-amplification manipulation of amplification products without a significant effect on amplification itself. Alternately, more than two primers are used, where each primer introduces exogenous nucleotide sequence that allow post-amplification manipulation of amplification products without a significant effect on amplification itself. Primers for a particular embodiment may be designed by one of skill in the art according to well-known principles, for example as disclosed in Dieffenbach and Dveksler ("General Concepts For PCR Primer Design" in, *PCR Primer: A Laboratory Manual*, Dieffenbach and Dveksler, eds., supra, the contents of which are hereby incorporated by reference in its entirety.)

In accordance with one aspect of the invention, primer length and sequence are of critical importance in designing the parameters of a successful amplification. The melting temperature ($T_m$) is the temperature at which a nucleic acid duplex "melts" to form two single strands, and $T_m$ increases as a function of its length and (G+C) content. Thus, the annealing temperature chosen for a particular embodiment of primer-directed amplification (e.g., PCR or RCA) depends on length and composition of the primer(s). In accordance with one aspect of the present invention, one of skill in the art can practice the methods disclosed herein using any annealing temperature ($T_a$) that permits generating single-stranded DNA molecules having defined sequence and length from genomic DNA or from RNA. Preferably, annealing temperature ($T_a$) is chosen that is about 5° C. below the lowest $T_m$ of the pair of primers being used in a particular embodiment.

Primers suitable for the methods disclosed herein should be sufficiently complex that the likelihood of annealing to sequences other than the chosen target is very low. Preferably, primers used to practice the present invention should be between approximately 17 to 28 bases in length (17-mer to 28-mer). By way of illustration, there is a one-in-four (1/4) chance of finding any base (A, G, C or T) in any given position in a DNA sequence; there is a one-in-sixteen (1/16) chance of finding any dinucleotide sequence (e.g., AG) in a DNA sequence, a one-in-256 (1/256) chance of finding a given four-base nucleotide sequence, and so on. A particular sixteen-base sequence will statistically be present only once in every approximately 4,294,967,296 bases, which is roughly the size of the human or maize genome. An oligonucleotide having at least 17 base pairs will show such specificity for its target sequence that 17-mer or longer primers are routinely used for amplification from genomic DNA or reverse-transcribed RNA (cDNA) of animals and plants. Preferably, base composition should be 50–60% (G+C), and primers should end (3') in a G or C, or CG or GC to prevent "breathing" of ends and increase efficiency of priming.

Primers suitable for the methods disclosed herein may be "degenerate" primers for use in degenerate PCR to amplify one or more target sequences. Degenerate PCR can be used to find one or more target sequences corresponding to a known protein sequence, or to find homologs, orthologs, or paralogs of a known sequence. The rules of codon usage are relied upon to design a set of degenerate primers that contains primers capable of binding to any of the possible target sequences of interest. Degenerate primers may be generated by synthesizing multiple primers with different nucleotides at positions known to be variable, and/or by introducing the nucleotide inosine at one or more positions known to be variable. Degenerate primers for a particular embodiment may be designed by one of skill in the art according to well-known principles, for example as disclosed in, *PCR Primer: A Laboratory Manual*, Dieffenbach and Dveksler, eds., supra, the contents of which are hereby incorporated by reference in its entirety.

In accordance with one aspect of the methods disclosed herein, "nested primers" may be included in some embodiments. Nested primers bind to sites on a template that occur within the target sequence of other primer pairs, and to sites on PCR products generated by the other primer pairs. The amplification products produced by nested primers will be smaller than the initial amplification products, and can be identified on the basis of their expected size. Thus, nested primers may be used to increase the specificity of amplification by ensuring that the desired target sequence is amplified to give a product that can be isolated from other amplification products. Nested primers for a particular embodiment may be designed by one of skill in the art according to well-known principles, for example as disclosed in *PCR Primer: A Laboratory Manual*, Dieffenbach and Dveksler, eds., supra, the contents of which are hereby incorporated by reference in its entirety.

It should be noted that too long a primer length may mean that even high annealing temperatures are not enough to prevent mismatch pairing and non-specific priming. One of skill in the art can determine the range of acceptable primer lengths for a given target region of interest, and can optimize primer design according to the needs of a particular embodiment.

In accordance with another aspect of the present invention, primers used to amplify templates are designed to introduce features into amplification products by means of introducing exogenous nucleotide sequence not found in the target nucleotide sequence. Exogenous sequences may introduce features including, but not limited to, restriction sites, modified nucleotides, promoter sequences, inverted repeats, and other non-template 5' extensions that allow post amplification manipulation of amplification products without a significant effect on the amplification itself. Preferably, the exogenous sequences are 5' ("upstream") of the primer sequence involved in binding to the target nucleotide sequence. In a preferred embodiment, exogenous sequences introduce sites involved in restriction enzyme recognition, binding and cleavage. In an even more preferred embodiment, primers containing inverted repeats or other exogenous sequences are used to introduce self-complementarity at the ends of the amplification product, such that single-stranded amplification products may form secondary structures such as "hairpins" or loops. In another highly preferred embodiment, auxiliary oligonucleotides are added to bind to the exogenous sequence and thereby create the restriction digestion sites needed for trimming to the final size.

Use of Rolling Circle Amplification to Amplify Target Sequences

In accordance with another aspect of the present invention, an isothermal amplification method is used to generate amplification products including a region having the target nucleotide sequence. Preferably, the isothermal replication method is the "rolling circle amplification" (RCA) method. In one preferred embodiment, linear amplification of target sequences is performed using RCA. In another preferred embodiment, non-linear amplification target sequences is performed using RCA. Methods for carrying out RCA are well known in the art, particularly as disclosed by Lizardi et al. (Lizardi et al., 1998, *Nature Genet* 19: 225–232, and U.S. Pat. Nos. 5,854,033, 6,124,120, 6,143,495, 6,183,960, 6,210,884, 6,280,949, 6,287,824, the entire contents of each of which are hereby incorporated by reference in their entireties.) Advantageously, RCA is an isothermal method having high specificity and sensitivity for target sequences and a low level of nonspecific background signal, wherein the amount of amplified product is proportional to the number of target sites in the genomic DNA or cDNA template, and optionally wherein a ligation step can be manipulated to carry out allelic discrimination.

The first step in RCA amplification is creation of a circular molecule that contains a sequence complementary to the target sequence. A synthetic linear molecule has at its 3' and 5' ends sequences of typically 10 to 20 nucleotides that are complementary to the target. In one embodiment there is a gap between the two complementary regions when the linear molecule is hybridized to the target. The gap is filled by primer extension, and the two ends are ligated together to form the circle. In another embodiment, there is no gap, and only the ligation step is employed. In linear RCA amplification, a primer complementary to a sequence on the circularized single strand is added, and a processive polymerase makes a continuous copy of the circle. The result is a long single-stranded molecule containing many repeats of the sequence in the circle. The exogenous sequences in the circle are designed such that the long complementary single-stranded product contains restriction sites analogous to those contained in the primers for PCR amplification. Restriction sites are introduced on both sides of the desired single-stranded product. In another preferred embodiment, the restriction sites are created by the addition of an auxiliary oligonucleotides that binds to the exogenous sequence. In non-linear RCA amplification, a second primer complementary to the single strand product of the rolling circle amplification is also added. The products of non-linear RCA amplification are largely double-stranded, and the use of this option requires digestion or removal of one of the strands.

Amplification products generated by RCA may be double-stranded or single-stranded stranded, depending on the amplification strategy chosen for a particular embodiment.

Figure 2:
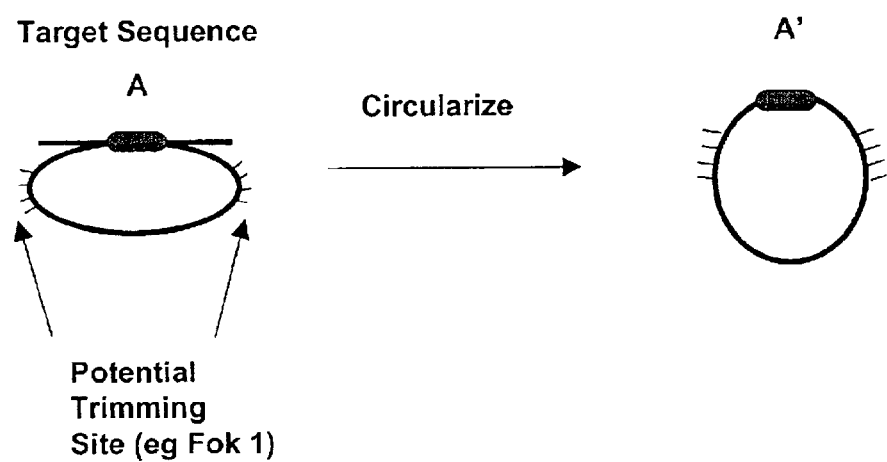
FIG. 2. A circularizable linear DNA molecule containing at its two ends sequences complementary to a target sequence A is hybridized to the template. If the sequence is designed so that the 3' and 5' ends are immediately adjacent, the molecule is circularized by DNA ligase. If a gap remains, it is filled by DNA polymerase, and the molecule is subsequently ligated into a circle. Exogenous sequences in the circularizable molecule are indicated as potential trimming sites. The circularized molecule contains the sequence A', which is complementary to the target sequence A.

Briefly, a circularizable single strand is hybridized to denatured DNA, then primer extension and/or ligation are used to generate a circular product in the presence of the target sequence, and finally, exonuclease digestion removes non-circular products. In a preferred embodiment, additional sequences are included in the circularizable single strand. In a particularly preferred embodiment, the circularizable molecule is designed and synthesized to include binding sites for restriction endonucleases and/or other enzymes involving in post-amplification manipulations such as trimming amplification products to generate single-stranded DNA molecules of defined sequence and length (FIG. 2).

A ligation step circularizes a specially designed (synthesized) nucleic acid probe molecule, where this step is dependent on hybridization of the probe to a target sequence (FIG. 2) and the number of circular probe molecules formed in this step is proportional to the amount of target sequence present in a sample.

Figure 3:
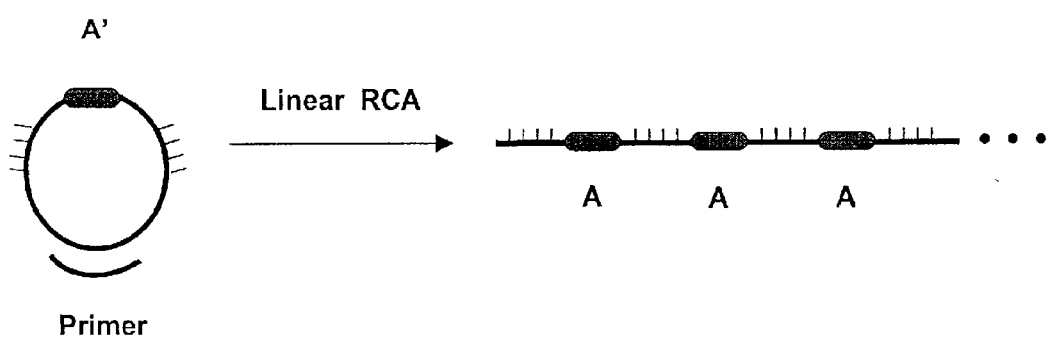
FIG. 3. Linear RCA amplification of the circular molecule. The single-stranded product contains the target sequence A, flanked on both sides by exogenous sequences designed for the trimming reaction.

The circular molecule is then amplified using rolling circle replication of the circularized probe, where a single round of amplification using rolling circle replication results in a large amplification of the circularized probe sequences. In one preferred embodiment, the circular molecule is amplified in exponential mode. In another preferred embodiment, the circular molecule is amplified in linear mode (FIG. 3). Advantageously, rolling circle amplification of probes is orders of magnitude greater than a single cycle of PCR or other amplification techniques in which each cycle is limited to a doubling of the number of copies of a target sequence.

Preferably, the circular molecule is amplified in exponential mode and one of the two primers is protected against 5'-exonuclease digestion using, e.g., 5'-5' linkage. Alternatively, one primer can be targeted for digestion by 5' phosphorylation. In such a preferred embodiment, 5'-exonuclease digestion of the product of exponential RCA leaves a protected, long single-stranded molecule capable of binding auxiliary oligonucleotides, and restriction cleavage is carried out as provided in the present disclosure to generate a single-stranded DNA molecule having defined sequence and length (FIG. 4).

Figure 4:
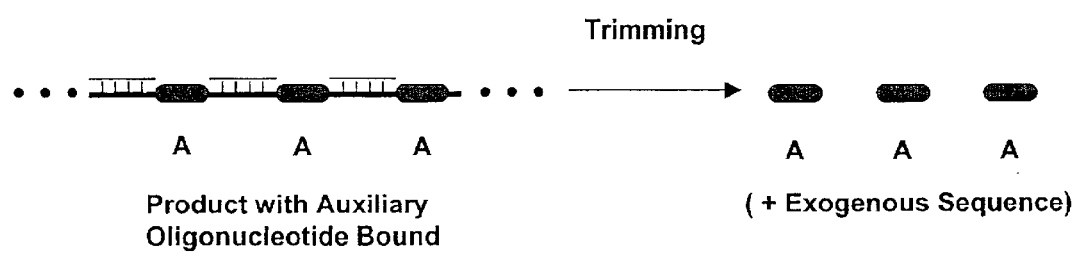
FIG. 4. Illustration of trimming by restriction digestion at sites formed by addition of auxiliary oligonucleotides complementary to the exogenous sequences in the single-stranded product.

Alternately, the circular molecule is amplified in linear mode and the long single-stranded product is trimmed as provided in the present disclosure and auxiliary oligonucleotides are added to provide regions of double-stranded DNA for recognition, binding, and/or cleavage sites for trimming enzymes (FIG. 4).

Optionally, an additional amplification operation can be performed on the DNA produced by RCA. Since the amount of amplified product is directly proportional to the amount of target sequence present in a sample, quantitative measurements of product reliably represent the amount of a target sequence in a sample.

In one embodiment, RCA using two probes (primers) gives rise to linear double-stranded amplification products.

In another embodiment, RCA in a linear mode gives rise to single-stranded amplification products. A circularizable probe can be ligated into a "padlock" configuration using a single primer or gap-filling nucleotides, where RCA of a "padlock probe" catalyzed by a strand-displacing DNA polymerase generates a single-stranded amplification product that includes the target nucleotide sequence.

In yet another embodiment, RCA can also be carried out using two primers in a "hyperbranched" mode, known as HRCA, to produce double-stranded amplification products that include the target nucleotide sequence. In multiplex assays, primer oligonucleotides used for DNA replication can be the same oligonucleotides used for all probes.

Probes and Primers for Use in RCA

Figure 5:
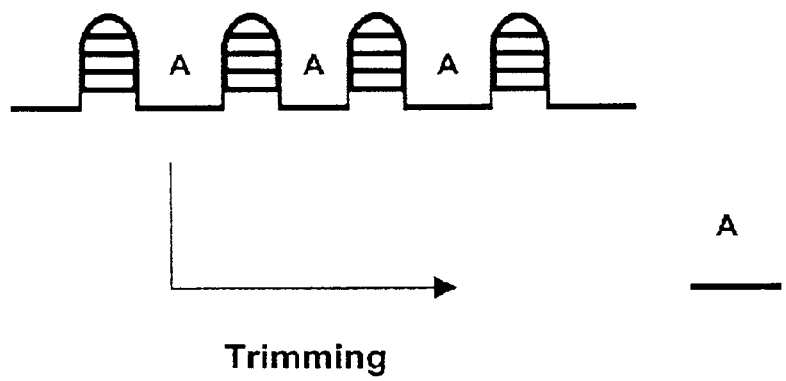
FIG. 5. Illustration of trimming by restriction digestion at hairpin helical sites encoded by the exogenous sequences in the circularizable molecule.

In accordance with another aspect of the present invention, probes and primers used to amplify templates by the RCA method are designed to introduce features into amplification products by means of introducing exogenous nucleotide sequence not found in the target nucleotide sequence. Exogenous sequences may introduce features including, but not limited to, restriction sites, promoter sequences, inverted repeats, and other non-template 5' extensions that allow post amplification manipulation of amplification products without a significant effect on the amplification itself. Alternately, some modes of RCA produce amplification products having alternating iterations (tandem repeats) of the target nucleotide sequence and the exogenous sequence introduced by probes or primers, such that the exogenous nucleotide sequence is located between copies of target nucleotide sequence. In a preferred embodiment, exogenous nucleotide sequences introduce sites involved in trimming single-stranded amplification products by restriction enzymes in conjunction with auxiliary oligonucleotides. In another preferred embodiment, primers and probes containing inverted repeats or other exogenous sequences are used to introduce self-complementarity at the ends of the amplification product, such that single-stranded amplification products may form secondary structures such as "hairpins" or loops (FIG. 5).

Conversion of Double-stranded Amplification Products to Single-stranded DNA

In accordance with another aspect of the present invention, double-stranded amplification products are converted to single-stranded amplification products. Double-stranded amplification products are composed of double-stranded DNA, and single-stranded amplification products are composed of single-stranded DNA, where the DNA strands may include modifications such as phosphorylation, cross-linking groups, or modified bases such as phosphorothioate nucleotide derivatives, as well as other modifications that may be chosen for a particular embodiment by one of skill in the art. Preferably, double-stranded DNA is converted to single-stranded DNA using one or more digestion methods. Advantageously, double-stranded amplification products are digested to provide single-stranded amplification products that can be further manipulated in the same reaction vessel, if desired. In one embodiment, digestion requires that one strand of the double-stranded amplification product contain a chemical modification that either (i) promotes selective digestion or the modified strand, or (ii) inhibits digestion of the modified strand, where such inhibition promotes digestion of the unprotected complementary strand. In another embodiment, digestion of double-stranded amplification products may include simultaneously promoting selective digestion of one strand and inhibiting digestion of the other strand, advantageously to increase the selectively of the digestion step.

In accordance with one aspect of the present invention, at least one primer is resistant to exonuclease digestion, preferably 5'→3' exonuclease digestion. Digestion-resistant primers or probes can be prepared as described in the art, e.g., in U.S. Pat. No. 5,518,900 to Nikiforov et al. Exonuclease-resistant exogenous nucleotide sequences are introduced into amplification products using amplification methods disclosed herein. In one preferred embodiment, PCR or RCA using two primers is carried out in which one primer is resistant to exonuclease digestion. In another preferred embodiment, probes used for RCA can be designed and synthesized to introduce exogenous nucleotide sequence that is resistant to nuclease digestion, preferably 5'→3' exonuclease digestion.

Suitable enzymes for carrying out digestion of double-stranded amplification products in accordance with the method disclosed herein include T7 exonuclease, lambda (λ) exonuclease, exonuclease m, and other enzymes that may be identified by one of skill in the art as appropriate for a particular embodiment. Enzymes for digesting double-stranded amplification products may be isolated from naturally occurring sources, or may be recombinantly produced.

In one embodiment, T7 exonuclease activity is blocked by introducing a 5'-5' linkage in one strand, thereby inhibiting digestion of the blocked strand and promoting digestion of the unblocked strand. In another embodiment, T7 exonuclease activity is blocked by incorporating phosphorothioate nucleotide derivatives into one strand, thereby inhibiting digestion of the blocked strand and promoting digestion of the unblocked strand. In another embodiment, lambda (λ) exonuclease selectively digests one strand of a double-stranded DNA duplex from a 5' phosphorylated end leaving the complementary strand intact. A 5' phosphate group is introduced to only one of the two strands during amplification by using one phosphorylated primer and one nonphosphorylated primer, for example as disclosed in Higuchi et al (1989, *Nuc Acids Res* 17: 5865). The phosphorylated strand is then removed by treatment with lambda exonuclease, generating single-stranded DNA.

In another preferred embodiment, double-stranded amplification products were converted to single-stranded DNA using lambda exonuclease. After amplification of genomic DNA, the 77 base pair double-stranded amplification products were incubated with lambda exonuclease. When the digestion products were separated on an agarose gel, very little 77-nucleotide (nt) single-stranded DNA was seen when no lambda exonuclease was added, and increasing amounts of single-stranded 77-nt DNA was seen with increasing amounts of lambda exonuclease.

In yet another embodiment, incorporation of alphaP-borane 2'-deoxynucleoside 5'-triphosphates (dNT(b)Ps) blocks the action of exonuclease, as described, e.g., by Porter et al. (1997, *Nucleic Acids Res.* 25:1611–7).

In accordance with another aspect of the invention, non-enzymatic methods may be employed to recover single-stranded DNA from double-stranded amplification products. In one representative embodiment, biotinylated nucleotides are utilized during the amplification step, and biotinylated amplification products can then be captured using a (strept) avidin-coated solid support including but not limited to (strept)avidin-coated beads or surfaces. Once the biotinylated amplification product is bound to the solid support, the sample is subjected to alkaline conditions, or heat, or other conditions suitable to breaking the hydrogen bonds between the two strands. In this embodiment, the nonbiotinylated strand is recovered (eluted) and can be trimmed or otherwise manipulated in accordance with the method disclosed herein.

Trimming Single-stranded DNA

In accordance with another aspect of the present invention, at least one single-stranded amplification product is trimmed to produce at least one DNA molecule having the desired nucleotide sequence and length, generating a single-stranded DNA molecule of defined sequence and length. Amplification products may be trimmed using restriction endonucleases that cleave at a site distant from their recognition site or may be trimmed using restriction endonucleases that recognize, bind, and cleave at the same site. Preferably, the single-stranded DNA molecule of defined sequence and length generated by trimming is a short molecule having a length from 5 to 50 nucleotides, more preferably a molecule having a length of 10 to 45 nucleotides, even more preferably a molecule having a length of 15 to 40 nucleotides. In accordance with the methods disclosed herein, a single-stranded DNA molecule of defined sequence and length may advantageously be 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In accordance with one aspect of the present invention, restriction endonucleases that cleave remotely by recognizing one site and cleaving at another site can be utilized trim the single-stranded amplification product to generate a short DNA molecule of defined sequence and length. Preferably, the remote-acting restriction endonucleases are Class IIS restriction endonucleases that cleave double-stranded DNA at precise distances from the recognition sites. (Szybalski, 1985, *Gene* 40: 169–173; Podhajska and Szybalski, 1985, *Gene* 40: 175–182; Sugisaki and Kanazawa, 1981, *Gene* 16: 73–78) Because of their remote action, these enzymes are also known as "shifters." (Szybalski, 1985, *Gene* 40: 169–173) More preferably, the Class IIS restriction endonucleases used to trim DNA include, but are not limited to, BbvI, BbvII, BinI, FokI, HgaI, HphI, MboII, MnlI, SfaNI, TaqII, Tth111II, and MluI. (Szybalski (1985) *Gene* 40: 169–173; Sugisaki and Kanazawa (1981) *Gene* 16: 73–78) Advantageously, remote-acting enzymes such as Class IIS restriction endonucleases can be used to trim a DNA molecule even more than when the trimming enzyme binds and cleaves at the same site. Even more advantageously, remote-acting enzymes can be used to generate DNA molecules containing only the desired nucleotide sequence and no unwanted or exogenous sequence.

In one preferred embodiment, FokI is used to trim DNA. FokI was isolated from *Flavobacterium okeanokoites* (Sugisaki and Kanazawa, 1981, *Gene* 16: 73–78) FokI uses the a double-stranded recognition site domain containing the sequence GGATG and its complement, and cleaves in a "staggered" pattern 9 and 13 base-pairs away from the recognition site. (Syzbalski, 1985, *Gene* 40: 169–173; see also, WO0175180) MluI introduces double-strand cleavages at unique sequences that are completely two-fold rotationally symmetric like most type II restriction endonucleases. (Sugisaki and Kanazawa, 1981, *Gene* 16:73–78)

Figure 6:
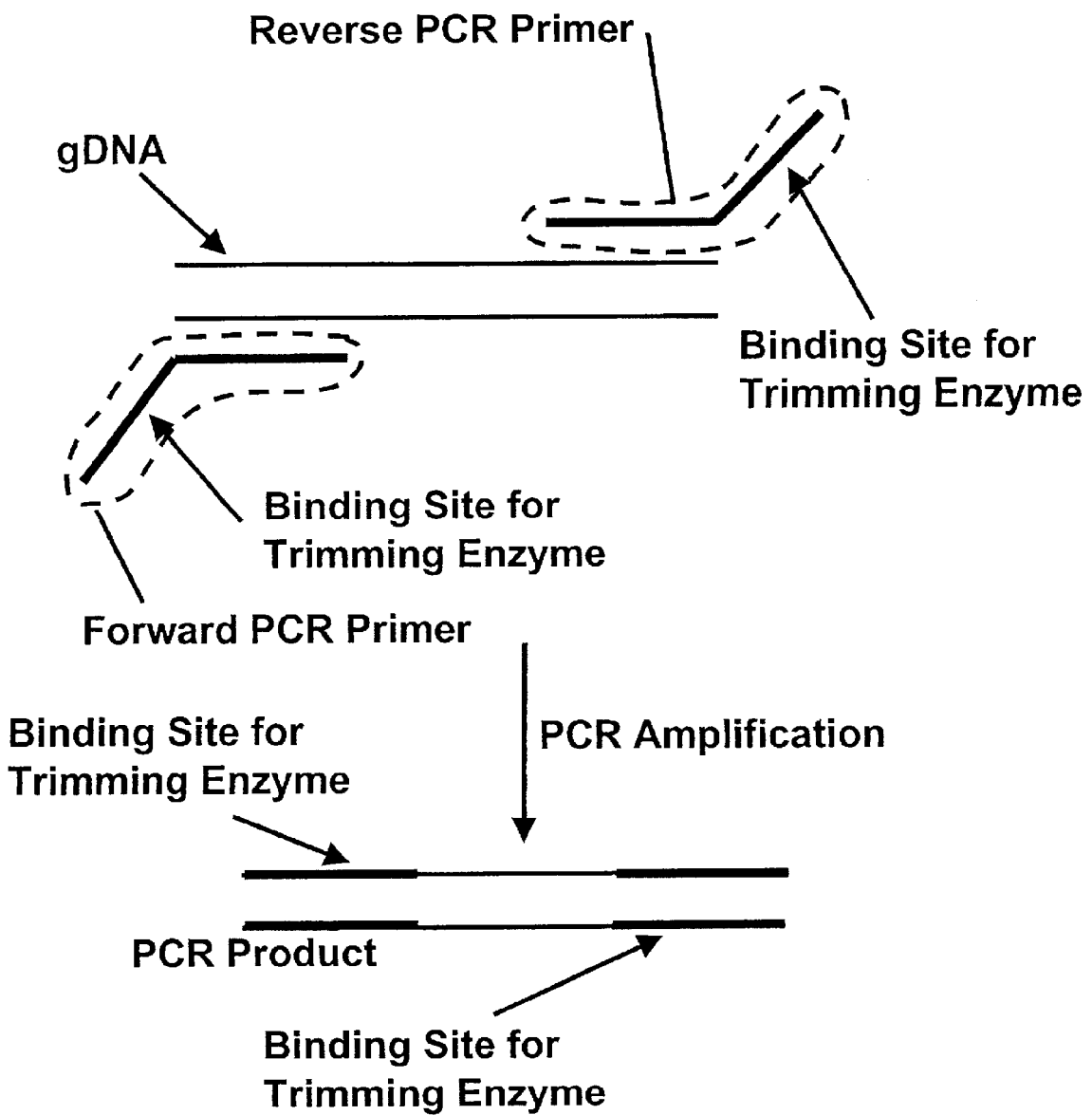
FIG. 6. Illustration of PCR probes used to introduce exogenous sequences that encode restriction sites for the trimming reaction. The double-stranded amplification products is shown.
Figure 7:
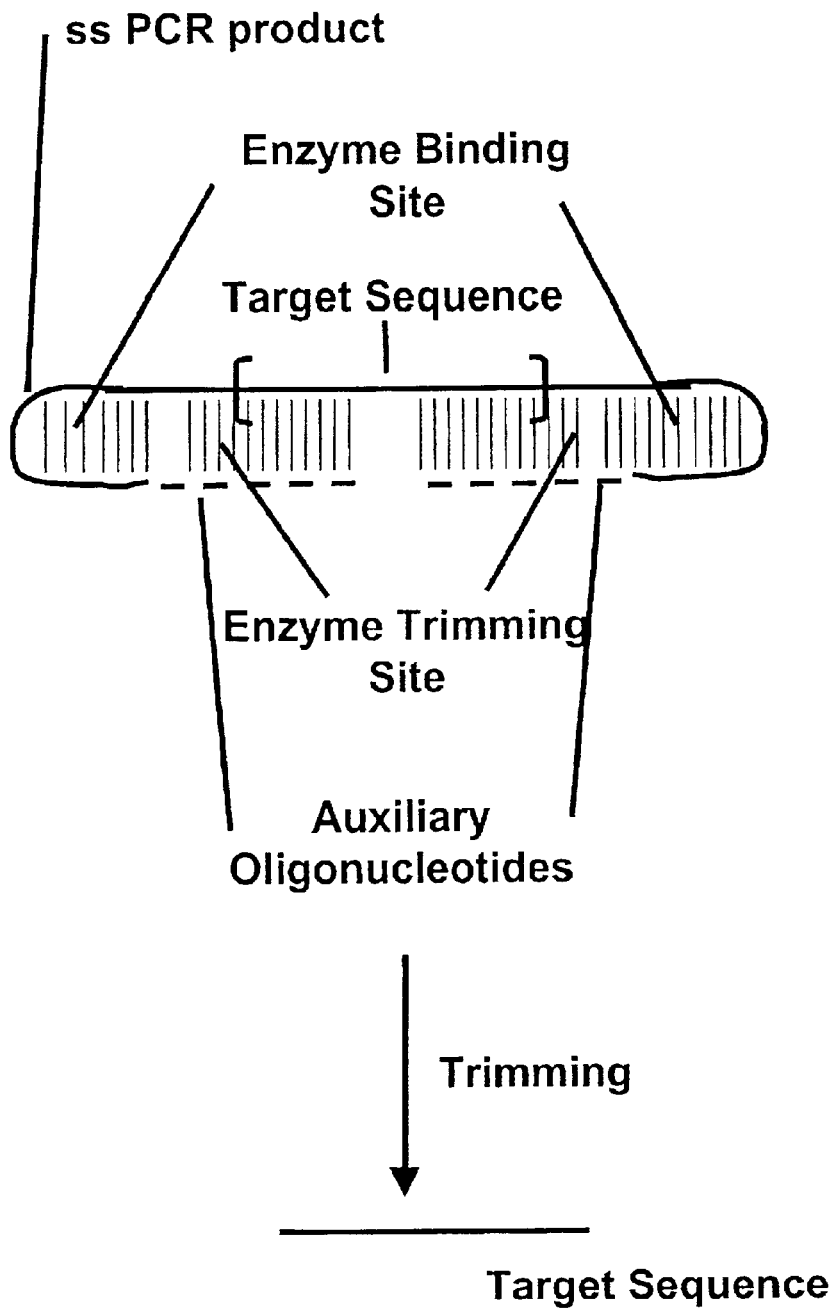
FIG. 7. Illustration of the use of auxiliary oligonucleotides to provide a double helical substrate for a Type IIs restriction enzyme (e.g., FokI). In this case, the enzyme recognition sequence is encoded in hairpin helical structures that derives from exogenous sequences in the primers.

In one preferred embodiment, single-stranded amplification products having terminal hairpin-forming regions are trimmed using FokI. It is necessary to introduce a FokI binding site into the amplification product and provide a double-stranded substrate for FokI binding and cleavage. In an especially preferred embodiment, the binding site is provided as part of the nucleotide sequence of the PCR primers or RCA primers/probes used to amplify templates, to introduce at least one appropriate site into the amplification product, as illustrated in FIG. 6. In one embodiment, primers are designed to produce a double-stranded FokI substrate as follows: forward and reverse primers for PCR have complementary inverted regions such that the single-stranded amplification product generated by digesting a double-stranded amplification product of the amplification would fold back at both ends to form a helix of 8–16 bp containing a FokI binding site, as illustrated by the diagram of FIG. 7. In such an embodiment, auxiliary oligonucleotides that hybridize to the region where cleavage is desired (see FIG. 7) must be supplied in order to provide a region of double-stranded substrate for cleavage. In the present embodiment, FokI cleaves 9 bases from one recognition site and 13 bases from the other. It is understood that such a protocol is not limited to use with FokI, as one of skill in the art could design primers that would introduce exogenous nucleotide sequences including recognition sites for any restriction endonuclease that cleaves at a distance from its recognition site.

In another preferred embodiment, linear primers were used to generate a FokI substrate, preferably when it is not feasible to design primers with tandem repeats as hairpin-forming sequences that generate a complete recognition site. In embodiments using linear primers, primers contain only the top strand sequence of a FokI restriction site, or that of another restriction endonuclease that cleaves at a site distant from its recognition site. In a particularly preferred embodiment, single-stranded amplification product were produced in accordance with the methods of the present invention, and auxiliary oligonucleotides were added that overlap the single strand in two locations, such that one oligonucleotide formed a double strand at the trimming (cleavage) site and another provided the second half of the FokI recognition site. With double-stranded DNA available at recognition and cleavage sites, Fokd or a similar restriction endonuclease can trim the DNA molecule to generate a single-stranded molecule of defined length and sequence. It in understood that linear primers for use in amplification, and auxiliary oligonucleotides for use in providing localized double-stranded DNA, could be designed by one of skill in the art in light of the needs, constraints, materials available, or other factors that may be relevant to circumstances of a particular embodiment.

In accordance with another aspect of the invention disclosed herein, restriction endonucleases that bind and cleave at the same site can be used to trim single-stranded amplification products to generate a short single-stranded DNA molecule of defined length and sequence. For example, Type II restriction enzymes bind at a recognition site and cleave within the restriction site; descriptions of the recognition sites and cleavage patterns of Type II enzymes can be found in the art. Preferably, Type II restriction endonucleases are utilized to trim single-stranded amplification products according to the methods disclosed herein. In one preferred embodiment, a restriction enzyme such as EcoR1, is used to trim the amplification product. Primers and/or probes can be designed and synthesized to include a restriction endonuclease binding site, e.g., an EcoR1 binding site.

Figure 8:
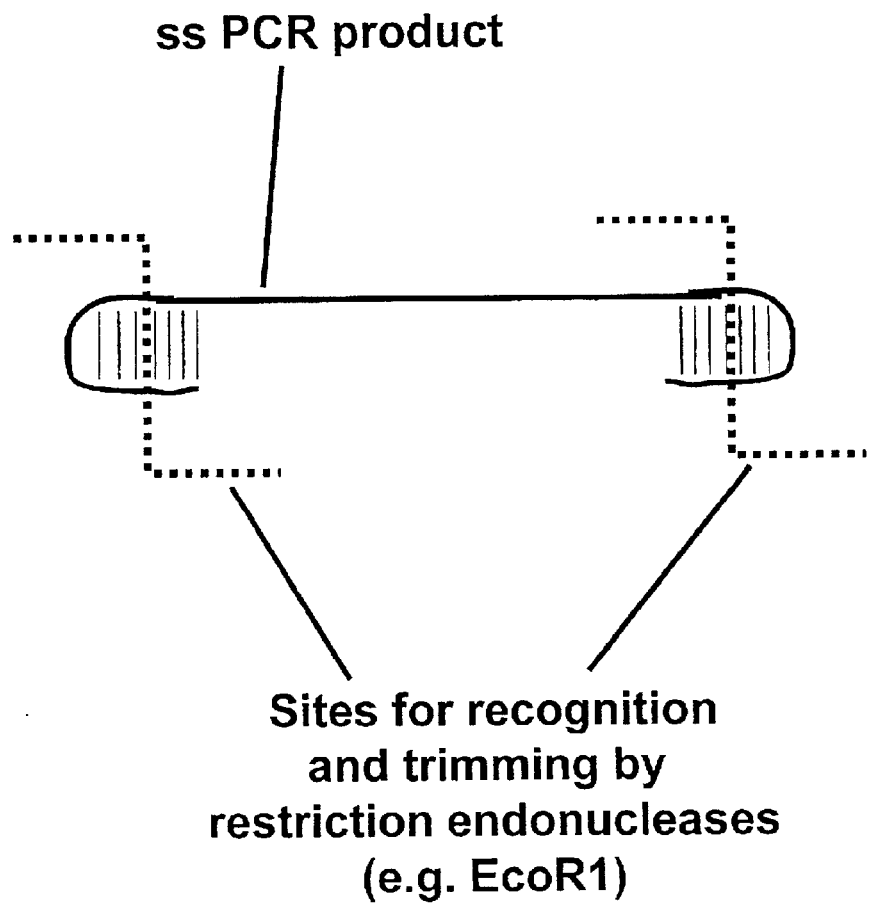
FIG. 8. Illustration of trimming by a Type II restriction enzyme (e.g., EcoRI), whose recognition sites are encoded in exogenous sequences in the primers.

In one preferred embodiment, the primers used in amplification include tandem inverted repeats encoding EcoRI binding sites, with the result that the ends of the single-stranded amplification product can fold back to form hairpin turns, thereby providing double-stranded DNA at the binding and trimming site. Advantageously, this approach does not require addition of auxiliary oligonucleotides to the single-stranded amplification product (FIG. 8).

In another preferred embodiment, linear primers containing a single copy of the restriction endonuclease recognition site are used in amplification, and auxiliary oligonucleotides including the restriction endonuclease site are added to the single-stranded amplification product to provide a localized region of double-stranded DNA for restriction endonuclease binding and trimming to release a short single-stranded DNA of defined sequence and length.

Use of a Nicking/cleaving Strategy to Generate Single Stranded DNA Molecules Having Defined Sequence and Length Another aspect of the invention provides methods for generating single stranded DNA molecules of defined sequence and length wherein the use of exonuclease to release a single strand of DNA and the use of auxiliary oligonucleotides to complete the cleavage site is not necessary. These methods produce an oligomer having the desired nucleotide sequence, generating a single stranded DNA molecule of defined sequence and length from a double stranded amplification product.

In one preferred embodiment, the exonuclease step is avoided by using a nicking enzyme at one end of the defined sequence and cleavage at the other end of the defined sequence, where the defined sequence is contained in a double-stranded amplification product. The oligomer having the defined sequence and lenght is separated from the remainder of the amplification product, which includes its complement and the primer duplexes of the amplification product, by heating under conditions that allow the oligomer to separate from its complement but leave the primer duplexes intact. Preferably, exogenous sequence introduced by a primer includes an addressable ligand such as biotin attached to the primer, and in one particularly preferred embodiment, the primer complexes are removed by attachment to magnetic beads carrying streptavidin that binds to biotin labels attached to the 5' end of at least one primer. Example 6 provides an illustrative example of this method.

Amplification of RNA to Generate Single-stranded DNA Molecules

In accordance with another aspect of the present invention, the methods disclosed and claimed herein may be used to amplify RNA templates to generate short single-stranded DNA molecules of defined sequence and length. RNA may be reversed-transcribed to generate cDNA which may be amplified using any suitable method including, but not limited to, PCR or RCA. Alternately, RCA may be used to amplify RNA directly.

For procedures that employ PCR, the RNA molecule of interest must be reverse-transcribed to provide a cDNA copy suitable for amplification. PCR amplification of a cDNA copy of the RNA of interest generates double-stranded DNA amplification products that must be converted to single-stranded products and trimmed according to aspects of the invention provided in the present disclosure.

In accordance with another aspect of the present invention, RCA may be used to amplify RNA directly, without conversion to cDNA, using RCA in linear or exponential mode. In one embodiment, the primers used to generate the rolling circle include at least one binding site for a trimming enzyme, such that exogenous nucleotide sequence including the binding site is incorporated into the amplification products during the amplification step. Double-stranded amplification products are converted to single-stranded amplification products that are trimmed to generate short single-stranded DNA molecules of defined sequence and length using any of the methods disclosed herein.

As provided in accordance with another aspect of the present invention, RCA can be used in the exponential mode to detect and amplify low copy number messenger RNAs or protein antigens. In a preferred embodiment, DNA microarray applications are developed that exploit signal enhancement by RCA for performing mRNA expression profiling at unprecedented sensitivity. In another preferred embodiment, methods for exponential amplification and in vitro expression of cDNA and genomic DNA fragments are provided, including but not limited to DNA strand displacement reactions that permit isothermal amplification of clones derived from single DNA molecules.

Use of Methods for Generating Single-stranded DNA Molecules

In accordance with another aspect of the present invention, methods for generating single-stranded DNA molecules of defined sequence and length from template containing a target nucleotide sequence as described herein, may be used to identify an organism or individual. A sample including template is obtained from an organism or individual, or from a multiplicity of organisms or individuals, where the template contains at least one target nucleotide sequence, and the template may be genomic DNA, cDNA, or RNA. Template is amplified using one or more specially designed primers or probes, conversion of double-stranded amplification products into single-stranded amplification products is carried out if necessary, and single-stranded amplification products are trimmed as described herein to yield the desired set of DNA molecules of defined sequence and length, in accordance with the methods of the present invention as described herein. In one embodiment, the primers are chosen so that the sizes of the molecules in the set of single stranded DNA molecules are sufficient to identify a specific organism, where size may be measured as mass, nucleotide sequence, or length of the DNA molecule. In a preferred embodiment, template is amplified using specially designed primers or probes and double-stranded amplification products are produced, then the double-stranded amplification products are converted into single-stranded amplification products, and single-stranded amplification products are trimmed as described herein to yield the desired set of DNA molecules of defined sequence and length. In another preferred embodiment, template is amplified using specially designed primers or probes and single-stranded amplification products are produced, then the single-stranded amplification products are trimmed as described herein to yield the desired DNA molecule of defined sequence and length. The mass or nucleotide sequence of each single-stranded DNA molecule having the desired sequence and length can be determined, for example using mass spectroscopy to rapidly determine mass and/or nucleotide sequence, and the mass or nucleotide sequence can be used to identify an organism or an individual using tools available to one of skill in the art. In another embodiment, this method can be carried out using template from a multiplicity of organisms or individuals, the nucleotide sequence of each of a multiplicity of single-stranded amplification products is determined, and the masses or nucleotide sequences can be used to identify multiple organisms or individuals. In yet another embodiment, this method can be carried out using a sample from a multiplicity of organisms and individuals wherein the sample including template is obtained from a mixture of organisms or individuals, or alternately wherein multiple samples, each sample obtained from a single organism or individual, are pooled to create a single pooled sample for amplification, conversion, trimming, sequencing, and identification in accordance with the methods described herein.

EXAMPLES

Example 1

Sample Preparation and Amplification

Materials

Oligonucleotides were synthesized with phosphoramidites purchased from Glen Research. All enzymes were purchased from New England Biolabs Inc. (Beverly, Mass.), except for Taq DNA polymerase (Stratagene, La Jolla Calif.). Deoxyribonucleotide triphosphates (dNTP's) were also acquired from Stratagene. $\gamma$-$^{32}$P-ATP (3000 Ci/mmol) was obtained from Perkin Elmer Life Sciences (Boston, Mass.). Microquick spin columns were purchased from Roche Molecular Biochemicals (Indianapolis, Ind.). Oligonucleotides were synthesized using the phosporamidite method on an ABI 394 DNA synthesizer.

Preparation of Genomic DNA from Blood/cell Lines or Tissue Samples

Genomic DNA was prepared according to manufacturer's instructions using QuiAamp Blood DNA and QiAamp DNA kits (Quiagen, Valencia, Calif.). Similar kits are available for processing RNA.

Polymerase Chain Reaction

PCR conditions were optimized for desired yield and specific template, quantity of genomic DNA, primers, and other components of the reaction, as well as the cycling conditions and specific temperatures. A specific illustration of optimized PCR conditions is found below. In certain conditions, it was necessary to inactivate components of the PCR reaction, for example by the use of phosphatase to inactivate dNTPs, or protease to inactivate DNA polymerase. (Werle et al., 1994, *Nucleic Acids Res* 22:4354–5)

Example 2

Generation of Single Strand DNA, Trimming, and Hybridization to Complementary Strand Generation of Single Strand DNA by Lambda Exonuclease Digestion The PCR reaction of Example 1 was supplemented to a final concentration of 50 μg/ml Bovine Serum Albumin (BSA) prior to removal of the targeted (5' phosphorylated) DNA strand by lambda exonuclease according to the manufacturer's protocol, and recovery of the desired single-stranded DNA, if BSA was not added to the PCR reaction buffer. Concentration and incubation times varied, depending on yield from the PCR reaction (see specific example below). Heat inactivation of the enzyme for 10 minutes at 75° C. was desirable prior to subsequent steps.

Trimming of Single Stranded DNA to Desired Size

Auxiliary oligonucleotides in a compatible buffer were provided to generate the double-stranded restriction endonuclease recognition site. The amount of enzyme and incubation conditions varied depending on amount of single-stranded product (see specific example below). To increase storage stability of final product at −20° C., heat inactivation for 20 minutes at 65° C. is recommended.

Hybridization to Complementary Strand

The resulting single-stranded DNA was hybridized to its radioactive complementary strand for visualization after gel electrophoretic separation. Alternatively, it can be used for electrochemical SNP detection when allowed to hybridize to a test sequence immobilized to a solid support.

Example 3

Amplification of the Region of the S241→F of the p53 Tumor Suppressor Gene

Polymerase Chain Reaction 25 ng of gDNA (from blood or cells) was amplified in a PCR reaction in a buffer containing 67 mM Glycine-KOH (pH 9.4), 2.5 mM $MgCl_2$, 50 μg/ml BSA, 0.625 Units Taq DNA polymerase, 0.2 mM dNTP's, and 0.2 μM of each primer, using the following A, protocol: 94° C. 2 minutes, followed by 30 cycles of 30 seconds at 94° C. 30 seconds at 64° C., and 30 seconds at 72° C. The following oligonucleotide primers were used:

Primer 26.1'P

5' P-ATA GGA TGG TTC ATG CCG CCC ATG
       CA 3'                                       (SEQ ID NO: 1)

Primer 27.2

5' TGG GGA TGA ACT ACA TGT GTA ACA
       GTT 3'                                      (SEQ ID NO: 2)

Lambda Exonuclease Digestion 2.5 units lambda exonuclease were added to the PCR reaction, followed by incubation for 20 minutes at 37°. The enzyme was inactivated by incubation for 10 minutes at 75° C.

Fok I Digestion

The digestion reaction contained 650 nM of each auxiliary oligonucleotide in 50 mM potassium acetate, 20 mM Tris-acetate, 10 mM magnesium acetate, 1 mM dithiothreitol, pH 7.9, added to the samples prior to incubation for 20 minutes at 37° C. with 4 units FokI. The enzyme was inactivated by incubation at 65° C. for 20 minutes. The auxiliary oligonucleotides were:

(24.1') 5' TGT TAC ACA TGT AGT TCA TCC
       CCA 3'                                    (SEQ ID NO: 3)

(26.1') 5' ATA GGA TGG TTC ATG CCG CCC
       ATG CA 3'                                 (SEQ ED NO:4)

Hybridization to Complementary Strand

The single-stranded 17-mer single-stranded DNA product was hybridized to the test sequence (17.1') 5' $^{32}$P-ATG CAG GAA CTG TTA CA 3' (SEQ ID NO: 5) by 15 minute incubation at room temperature. The test sequence 17.1' (SEQ ID NO: 5) was phosphorylated by end-labeling, as follows: 0.5 μM oligonucleotide was incubated for one hour at 37° C. with 20 μCi of γ-$^{32}$P-ATP (3000 Ci/mmol) and 10 units T4 polynucleotide kinase in 70 mM Tris-HCl, pH 7.6, 10 mM $MgCl_2$, 5 mM dithiothreitol. To quantify the amount of product made, reactions were spiked with unphosphorylated test sequence 17.1' and the fraction of the 7-mer duplex was estimated by comparing the intensity of excess $^{32}$P single-stranded 17-mer to the total mixture (duplex+excess probe).

Example 4

Multiplexing. Detection of Three SNPs in the p53 Tumor Suppressor Gene

This experiment is analogous to Example 3 above, except that three (or more) sequences are amplified simultaneously, in the same tube. The primers must be designed for length such that the optimum PCR temperatures are similar. For a mixture of SNPs constituting C176F, S241F and R248W the following primers and auxiliary oligonucleolides are used:

For SNP C176F

PCR Primers

Primer 27.6

5' GAT GGA TGA CGG AGG TTG TGA GGC
       GCT 3'                                      (SEQ ID NO: 6)

Primer 26.5'p

5' P-ATA GGA TGG CAG CGC TCA TGG TGG
       GG3'                                        (SEQ ID NO: 7)

Auxiliary Oligonucleotides (24.5') 5' GCC TCA CAA CCT CCG TCA TCC
       ATC 3'                                    (SEQ ID NO: 8)

(26.5') 5' ATA GGA TGG CAG CGC TCA TGG
       TGG GG3'                                (SEQ ID NO:9)

For SNP S241F

Same primers as in Example 3, above: primer 26.1'P (SEQ ID NO: 1) and primer 27.2 (SEQ ID NO: 2).

For SNP R273H

PCR Primers

Primer 27.4

5' ATA GGA TGA CGG AAC AGC TTT GAG
       GTG 3'                                    (SEQ ID NO: 10)

Primer 26.3'p

5' P-ATA GGA TGC CAG GAC AGG CAC AAA
       CA 3'                                       (SEQ ID NO: 11)

Auxiliary Oligonucleotides (24.3') 5' CTC AAA GCT GTT CCG TCA TCC
TAT 3' (SEQ ID NO: 12)

(26.3') 5' ATA GGA TGC CAG GAC AGG CAC
AAA CA 3' (SEQ ID NO: 13)

The enzymatic reactions and assay are carried out as in Example 3, above. It was observed that SNPs that are so closely spaced that their primer sites overlap cannot be amplified in the same tube.

Example 5

Linear RCA Amplification of DNA to Produce Single Strand Fragments of Defined Size The following example presents the use of a synthetic target which is phosphorylated at the 5' end, if using lambda exonuclease, or unmodified if using T7 exonuclease.
Target DNA Sequence 30.1P

5' P-CAG CTT TGA GGT GCG TGT TTG TGC
CTG TCC 3' (SEQ ID NO: 14)

is hybridized to padlock probe sequence 70.1P:

5' P-GCA CCT CAA AGC TGC GCA TCC CAT CAG ATA GCG
AGT CGA CGT GAG GAT GTA CGT GGA CAG GCA CA
AAC AC 3' (SEQ ID NO: 15).

The padlock probe sequence 70.IP (SEQ ID NO: 15) has a region of complementarity to the target sequence (SEQ ID NO 14), in addition to Fok I restriction sites spanning the target sequence and a nonhomologous sequence that completes the padlock and contains primer recognition sites for a strand displacing polymerase such as phi29 DNA polymerase. The ligation and polymerization process are described, for example, by Zhong et al., (2001, *Proc. Nat. Acad. Sci.* 98:3940–3945). The target DNA sequence 30.1 P (SEQ ID NO; 14) and padlock probe 70.1P (SEQ ID NO: 15) are hybridized in 1x Taq DNA Ligase buffer (New England Biolabs, Beverly Mass.). Ligation proceeds at 45° C., 15 minutes with the addition of Taq DNA ligase. After heat inactivation at 70° C. for 10 minutes, the buffer is exchanged for exonuclease buffer by a size-exclusion column.

In the control reaction, target 30.2P

5' P-CAG CTT TGA GGT GCC TGT TTG TGC
CTG TCC 3' (SEQ ID NO: 16)

is used, which contains a mismatch at the ligation site, such that the mismatch inhibits circularization of the padlock probe 70.1P (SEQ ID NO: 15). Alternatively, ligation can be inhibited by treating the padlock probe 70.1P with a phosphatase, or by using an unmodified version of the 70.1 sequence.

Addition of lambda exonuclease (New England Biolabs, Beverly Mass.) digests both the target sequence and the uncircularized probe. The circularized padlock probe remains intact (undigested by lambda exonuclease) and can be used as template for to RCA. Primers that serve as template for the DNA polymerase are complementary to regions of the nonhomologous sequence of the circularized padlock. The product of the linear RCA is hybridized with auxiliary oligonucleotides 24.1 LOCK

5' ATG GGA TGC GCA GCT TTG AGG
TGC 3' (SEQ ID NO: 17)

and
24.2 LOCK

5' TGT GCC TGT CCA CGT ACA TCC
TCA 3' (SEQ ID NO: 18)

which completes the double-stranded template for FokI digestion. The product that results from this reaction is a single-stranded 15-mer:

5' GAG GTG CGT GTT TGT 3' (SEQ ID NO: 19).

Example 6

Preparation of Single-stranded DNA by a Nicking/cleaving Strategy

A double-stranded PCR product is produced according to methods described herein. This method produces an oligomer having the desired nucleotide sequence, thereby generating a single stranded DNA molecule of defined sequence and length in accordance with the methods of the present invention. The double-stranded amplification product is incubated with a nicking enzyme and a cleavage enzyme, such that the double-stranded amplification product is. nicked at one end of the defined sequence and cleaved at the other end of the defined sequence. In the present example, FokI binds to a recognition site on the exogeneous sequence introduced by one primer, and cuts at one end of the amplification product. The double-stranded amplification is nicked at the other end of the desired sequence.

The following primers can be used:

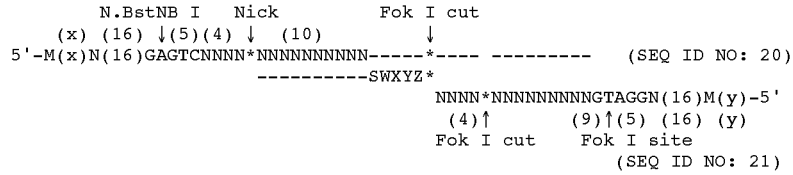

In this example, N represents nucleotides in the primer that are the same as in the genomic DNA. S represents a single nucleotide polymorphism (SNP), and W, X, Y, and Z represent nucleotides in the genomic DNA that are not found in either primer. The nucleotides designated M, exogenous nucleotide sequence(s) not in the target genomic DNA, can be included in the primers to increase the length of the double helical products that remain after nicking/cleavage. The present example shows that x(M) nucleotides can be added to the top fragment, and y(M) nucleotides can be added to the lower fragment.

Following the nicking/cleaving reaction, the oligonucleotide having the defined sequence is 15 nucleotides long. The left hand fragment (top) primer strand is 25+x nucleotides long, and the left hand (lower) strand is 35+x long. The right hand fragment (lower) primer strand is 30+y long, and the upper strand is 34+y long. The melting temperature of these structures depends on the length of the shorter arm, 25 and 30 in this example.

In the present example, the primer strand is labeled with biotin at the 5'-end. In order to separate the 15-mer having the defined sequence from the remainder of the amplification product, which includes its complement and the primer duplexes of the amplification product, the duplexes between the primer strand and the lower strand for the left primer (upper strand for the right primer) must remain intact when the 15-mer is melted from its complement. The nucleotides M on the left and right primers provide a mechanism for increasing the stability of these duplexes by increasing their lengths by amounts x and y respectively. In a multiplex mixture, all of the 15-mers having desired defined sequence would have to melt at lower temperature than any of the primer duplexes. The primer complexes are removed by attachment to magnetic beads carrying streptavidin that binds to biotin labels attached to the 5' end of at least one primer. It might be necessary to add EDTA to the mixture to chelate $Mg^{2+}$ in order to lower the stability of the 15-mer duplex to the stability range of the beads.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for generating a single-stranded DNA molecule of defined sequence and length comprising the following steps:
    amplification of a template comprising at least one target nucleotide sequence, said amplification being directed by at least one primer comprising at least one exogenous nucleotide sequence not present in the target nucleotide sequence, wherein said amplification generates a plurality of double-stranded amplification products comprising said at least one target nucleotide sequence and said at least one exogenous nucleotide sequence introduced by said at least one primer;
    conversion of each said double-stranded amplification product to a single-stranded amplification product; and
    trimming each said single-stranded amplification product to generate a single-stranded DNA molecule of defined sequence and length.

2. The method of claim 1, wherein polymerase chain reaction (PCR) is used for said amplification step.

3. The method of claim 1, wherein rolling circle amplification (RCA) is used for said amplification step.

4. The method of claim 1, wherein said amplification step is carried out in linear mode.

5. The method of claim 1, wherein said amplification step is carried out in non-linear mode.

6. The method of claim 1, wherein said template is genomic DNA or cDNA.

7. The method of claim 1, wherein said template is RNA.

8. The method of claim 1, wherein said at least one primer comprises at least one sequence having an addressable ligand attached thereto.

9. The method of claim 8, wherein said addressable ligand is biotin.

10. The method of claim 1, wherein said at least one exogenous nucleotide sequence introduced by said at least one primer comprises self-complementary sequences that form hairpin structures.

11. The method of claim 10, wherein said self-complementary sequences that form hairpin structures comprise at least one restriction enzyme recognition site for a restriction enzyme involved in said trimming step.

12. The method of claim 11, wherein said restriction enzyme involved in said trimming step is a Type II or Type IIS restriction enzyme.

13. The method of claim 12, wherein said Type II restriction enzyme is EcoRI.

14. The method of claim 12, wherein said Type IIS restriction enzyme is FokI.

15. The method of claim 1, further comprising adding at least one auxiliary oligonucleotide comprising at least one sequence complementary to at least a portion of said at least one exogenous nucleotide sequence introduced by said at least one primer, thereby forming at least one restriction enzyme recognition site for a restriction enzyme involved in said trimming step.

16. The method of claim 15, wherein said restriction enzyme involved in said trimming step is a Type II or Type IIS restriction enzyme.

17. The method of claim 16, wherein said Type II restriction enzyme is EcoRI.

18. The method of claim 16, wherein said Type IIS restriction enzyme is FokI.

19. The method of claim 15, wherein said at least one auxiliary oligonucleotide comprises at least one sequence having an addressable ligand attached thereto.

20. The method of claim 19, wherein said addressable ligand is biotin.

21. The method of claim 1, wherein said conversion step comprises digestion of one strand of said double-stranded amplification product comprising said at least one target nucleotide sequence and said at least one exogenous nucleotide sequence introduced by said at least one primer, using 5'→3' exonuclease.

22. The method of claim 21, wherein said 5'→3' exonuclease is T7 or lambda exonuclease.

23. The method of claim 21, wherein said at least one exogenous nucleotide sequence introduced by said at least one primer comprises modified nucleotides that confer resistance to digestion using 5'→3' exonuclease or sensitivity to digestion using 5'→3' exonuclease.

24. The method of claim 23, wherein said modified nucleotides confer resistance to digestion using 5'→3' exonuclease.

25. The method of claim 24, wherein said modified nucleotides are phosphorothioate derivatives.

26. The method of claim 23, wherein said modified nucleotides confer sensitivity to digestion using 5'→3' exonuclease.

27. The method of claim 26, wherein said modified nucleotides are phosphorylated.

28. The method of claim 1, wherein said single-stranded DNA molecule of defined sequence and length is between 10 and 100 nucleotides in length.

29. The method of claim 1, wherein said single-stranded DNA molecule of defined sequence and length is between 10 and 50 nucleotides in length.

30. The method of claim 1, wherein said single-stranded DNA molecule of defined sequence and length is 15 nucleotides in length.

31. The method of claim 1, wherein said single-stranded DNA molecule of defined sequence and length is 17 nucleotides in length.

32. The method of claim 1, wherein said single-stranded DNA molecule of defined sequence and length is 21 nucleotides in length.

33. The method of claim 1, wherein said single-stranded DNA molecule of defined sequence and length is 30 nucleotides in length.

34. A method for generating a single-stranded DNA molecule of defined sequence and length comprising the following steps:
    amplification of a template comprising at least one target nucleotide sequence, said amplification being directed by at least one primer comprising at least one exogenous nucleotide sequence not present in the target nucleotide sequence, wherein said amplification generates a plurality of double-stranded amplification products comprising said at least one target nucleotide sequence and said at least one exogenous nucleotide sequence introduced by said at least one primer;
    nicking each said double-stranded amplification product at one end of a defined sequence and cleaving said double-stranded amplification product at the other end of said defined sequence to generate a single-stranded DNA molecule of defined sequence and length; and
    separating said single-stranded DNA molecule of defined sequence and length from the remainder of the amplification product comprising the complement of said single-stranded DNA molecule and the primer duplexes of the amplification product.

35. The method of claim 34, wherein said single stranded DNA molecule of defined sequence and length is separated from the remainder of the amplification product by heating under conditions allowing said single stranded DNA molecule of defined sequence and length to separate from its complement while leaving the primer duplexes of the amplification product intact.

36. The method of claim 35 wherein said at least one primer has an addressable ligand attached thereto.

37. The method of claim 36, wherein said addressable ligand is biotin.

38. The method of claim 37, wherein said remainder of the amplification product comprising its complement and the primer duplexes of the amplification product are removed by attachment to magnetic beads carrying streptavidin that binds to said biotin attached to the 5' end of at least one primer.

39. A method for generating a single-stranded DNA molecule of defined sequence and length comprising:
    amplification of a template comprising at least one target nucleotide sequence, said amplification being directed by at least one primer containing at least one exogenous nucleotide sequence not present in the template, wherein said amplification generates a plurality of single-stranded amplification products comprising at least one target nucleotide sequence and at least one exogenous sequence introduced by said at least one primer; and
    trimming each said single-stranded amplification product to generate a single-stranded DNA molecule of defined sequence and length.

40. The method of claim 39 wherein said amplification is rolling circle amplification in the linear mode.

41. The method of claim 39 wherein said template is genomic DNA or cDNA.

42. The method of claim 39, wherein said template is RNA.

43. The method of claim 39, wherein said at least one primer comprises at least one sequence having an addressable ligand attached thereto.

44. The method of claim 43, wherein said addressable ligand is biotin.

45. The method of claim 39, wherein said at least one exogenous nucleotide sequence introduced by said at least one primer comprises self-complementary sequences that form hairpin structures.

46. The method of claim 45, wherein said self-complementary sequences that form hairpin structures comprise at least one restriction enzyme recognition site for a restriction enzyme involved in said trimming step.

47. The method of claim 46, wherein said restriction enzyme involved in said trimming step is a Type II or Type IIS restriction enzyme.

48. The method of claim 47, wherein said Type II restriction enzyme is EcoRI.

49. The method of claim 47, wherein said Type IIS restriction enzyme is FokI.

50. The method of claim 39 further comprising adding at least one auxiliary oligonucleotide comprising at least one sequence complementary to at least a portion of said at least one exogenous nucleotide sequence introduced by said at least one primer, thereby forming at least one restriction enzyme recognition site for a restriction enzyme involved in said trimming step.

51. The method of claim 50, wherein said restriction enzyme involved in said trimming step is a Type II or Type IIS restriction enzyme.

52. The method of claim 51, wherein said Type II restriction enzyme is EcoRI.

53. The method of claim 51, wherein said Type IIS restriction enzyme is FokI.

54. The method of claim 51, wherein said at least one auxiliary oligonucleotide comprises at least one sequence having an addressable ligand attached thereto.

55. The method of claim 54, wherein said addressable ligand is biotin.

56. A method for generating a single-stranded DNA molecule of defined sequence and length comprising:
    amplification of a template comprising at least one target nucleotide sequence, said amplification being directed by at least one primer containing at least one exogenous nucleotide sequence not present in the template, wherein said amplification generates a plurality of amplification products comprising at least one target nucleotide sequence and at least one exogenous sequence introduced by said at least one primer, wherein said amplification products comprise single-stranded or double-stranded amplification products and further wherein any said double-stranded amplification products may be converted to single-stranded amplification products; and
    trimming said single-stranded amplification products to generate at least one single-stranded DNA molecule of defined sequence and length.

57. A method for generating a single-stranded DNA molecule of defined sequence and length comprising:
    amplification of a single-strand of a target nucleic acid sequence, said amplification being directed by a nucleic acid primer complementary to at least a portion of a nucleic acid sequence comprising a nucleic acid sequence complementary to said target nucleic acid and at least one exogenous nucleic acid sequence, wherein said amplification generates a single-stranded nucleic acid concatamer comprising a plurality of single-stranded target nucleic acid sequences each separated by at least one exogenous nucleic acid sequence; and
    trimming said single-stranded nucleic acid concatamer to generate a plurality of single-stranded DNA molecules of defined sequence and length.

58. The method of claim 57, wherein each end of each single-stranded target nucleic acid present in said concatamer is flanked by an exogenous nucleic acid sequence.

59. The method of claim 57, wherein said nucleic acid primer comprises at least one sequence having an addressable ligand attached thereto.

60. The method of claim 59, wherein said addressable ligand is biotin.

61. The method of claim 57, wherein said at least one exogenous nucleotide sequence comprises self-complementary sequences that form hairpin structures.

62. The method of claim 61, wherein said self-complementary sequences that form hairpin structures comprise at least one restriction enzyme recognition site for a restriction enzyme involved in said trimming step.

63. The method of claim 62, wherein said restriction enzyme involved in said trimming step is a Type II or Type IIS restriction enzyme.

64. The method of claim 62, wherein said Type II restriction enzyme is EcoRI.

65. The method of claim 62, wherein said Type IIS restriction enzyme is FokI.

66. The method of claim 57, further comprising adding at least one auxiliary oligonucleotide comprising at least one sequence complementary to at least a portion of said at least one exogenous nucleotide sequence introduced by said at least one primer, thereby forming at least one restriction enzyme recognition site for a restriction enzyme involved in said trimming step.

67. The method of claim 58, wherein said restriction enzyme involved in said trimming step is a Type II or Type IIS restriction enzyme.

68. The method of claim 59, wherein said Type II restriction enzyme is EcoRI.

69. The method of claim 59, wherein said Type IIS restriction enzyme is FokI.

70. The method of claim 67, wherein said at least one auxiliary oligonucleotide comprises at least one sequence having an addressable ligand attached thereto.

71. The method of claim 70, wherein said addressable ligand is biotin.

* * * * *

SEQUENCE LISTING

```
<160> NUMBER OF SEQ ID NOS: 21

<210> SEQ ID NO 1
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)...(1)
<223> OTHER INFORMATION: n = modified adenosine

<400> SEQUENCE: 1
ntaggatggt tcatgccgcc catgca                                          26

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
tggggatgaa ctacatgtgt aacagtt                                         27

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
tgttacacat gtagttcatc ccca                                            24

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
ataggatggt tcatgccgcc catgca                                          26

<210> SEQ ID NO 5
<211> LENGTH: 17
```

```
<212> TYPE: DNA
<213> ORGANISM: Artificial Sequence
<220> FEATURE:
<223> OTHER INFORMATION: Test sequence 17.1
<220> FEATURE:
<221> NAME/KEY: modified_base
<222> LOCATION: (1)...(1)
<223> OTHER INFORMATION: n = modified adenosine

<400> SEQUENCE: 5
ntgcaggaac tgttaca                                                17

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
gatggatgac ggaggttgtg aggcgct                                     27

<210> SEQ ID NO 7
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (0)...(0)
<223> OTHER INFORMATION: n = modified adenosine

<400> SEQUENCE: 7
ntaggatggc agcgctcatg gtgggg                                      26

<210> SEQ ID NO 8
<211> LENGTH: 24
<212> TYPE: DNA
<213> ORGANISM: Artificial Sequence
<220> FEATURE:
<223> OTHER INFORMATION: Auxiliary oligonucleotide

<400> SEQUENCE: 8
gcctcacaac ctccgtcatc catc                                        24

<210> SEQ ID NO 9
<211> LENGTH: 26
<212> TYPE: DNA
<213> ORGANISM: Artificial Sequence
<220> FEATURE:
<223> OTHER INFORMATION: Auxiliary oligonucleotide

<400> SEQUENCE: 9
ataggatggc agcgctcatg gtgggg                                      26

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
ataggatgac ggaacagctt tgaggtg                                     27

<210> SEQ ID NO 11
```

```
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)...(1)
<223> OTHER INFORMATION: n = modified adenosine

<400> SEQUENCE: 11
ntaggatgcc aggacaggca caaaca                                   26

<210> SEQ ID NO 12
<211> LENGTH: 24
<212> TYPE: DNA
<213> ORGANISM: Artificial Sequence
<220> FEATURE:
<223> OTHER INFORMATION: Auxiliary oligonucleotide

<400> SEQUENCE: 12
ctcaaagctg ttccgtcatc ctat                                     24

<210> SEQ ID NO 13
<211> LENGTH: 26
<212> TYPE: DNA
<213> ORGANISM: Artificial Sequence
<220> FEATURE:
<223> OTHER INFORMATION: Auxiliary oligonucleotide

<400> SEQUENCE: 13
ataggatgcc aggacaggca caaaca                                   26

<210> SEQ ID NO 14
<211> LENGTH: 30
<212> TYPE: DNA
<213> ORGANISM: Artificial Sequence
<220> FEATURE:
<223> OTHER INFORMATION: Target sequence 30.1P
<220> FEATURE:
<221> NAME/KEY: modified_base
<222> LOCATION: (1)...(1)
<223> OTHER INFORMATION: n = modified cytosine

<400> SEQUENCE: 14
nagctttgag gtgcgtgttt gtgcctgtcc                               30

<210> SEQ ID NO 15
<211> LENGTH: 70
<212> TYPE: DNA
<213> ORGANISM: Artificial Sequence
<220> FEATURE:
<223> OTHER INFORMATION: Padlock probe sequence 70.1P
<220> FEATURE:
<221> NAME/KEY: modified_base
<222> LOCATION: (1)...(1)
<223> OTHER INFORMATION: n = modified guanosine

<400> SEQUENCE: 15
ncacctcaaa gctgcgcatc ccatcagata gcgagtcgac gtgaggatgt acgtggacag    60
gcacaaacac                                                    70

<210> SEQ ID NO 16
<211> LENGTH: 30
<212> TYPE: DNA
<213> ORGANISM: Artificial Sequence
<220> FEATURE:
<223> OTHER INFORMATION: Target sequence 30.2P
```

```
<220> FEATURE:
<221> NAME/KEY: modified_base
<222> LOCATION: (1)...(1)
<223> OTHER INFORMATION: n = modified cytosine

<400> SEQUENCE: 16
nagctttgag gtgcctgttt gtgcctgtcc                                              30

<210> SEQ ID NO 17
<211> LENGTH: 24
<212> TYPE: DNA
<213> ORGANISM: Artificial Sequence
<220> FEATURE:
<223> OTHER INFORMATION: Auxiliary oligonucleotide

<400> SEQUENCE: 17
atgggatgcg cagctttgag gtgc                                                    24

<210> SEQ ID NO 18
<211> LENGTH: 24
<212> TYPE: DNA
<213> ORGANISM: Artificial Sequence
<220> FEATURE:
<223> OTHER INFORMATION: Auxiliary oligonucleotide

<400> SEQUENCE: 18
tgtgcctgtc cacgtacatc ctca                                                    24

<210> SEQ ID NO 19
<211> LENGTH: 15
<212> TYPE: DNA
<213> ORGANISM: Artificial Sequence
<220> FEATURE:
<223> OTHER INFORMATION: Product of RCA amplification of target sequence
      30.2P

<400> SEQUENCE: 19
gaggtgcgtg tttgt                                                              15

<210> SEQ ID NO 20
<211> LENGTH: 19
<212> TYPE: DNA
<213> ORGANISM: Artificial Sequence
<220> FEATURE:
<223> OTHER INFORMATION: Primer
<220> FEATURE:
<223> OTHER INFORMATION: n = nucleotides in primer that are the same as
      in target genomic DNA

<400> SEQUENCE: 20
gagtcnnnnn nnnnnnnnn                                                          19

<210> SEQ ID NO 21
<211> LENGTH: 19
<212> TYPE: DNA
<213> ORGANISM: Artificial Sequence
<220> FEATURE:
<223> OTHER INFORMATION: Primer
<220> FEATURE:
<223> OTHER INFORMATION: n = nucleotides in primer that are the same as
      in target genomic DNA

<400> SEQUENCE: 21
nnnnnnnnnn nnngtaggn                                                          19
```